US007915578B2

(12) United States Patent
Case et al.

(10) Patent No.: US 7,915,578 B2
(45) Date of Patent: Mar. 29, 2011

(54) METHOD AND APPARATUS FOR CORRECTING SCATTERING IN SPECT IMAGING

(75) Inventors: James A. Case, Kansas City, MO (US); Bai-Ling Hsu, Olathe, KS (US); Timothy M. Bateman, Leawood, KS (US); S. James Cullom, Leawood, KS (US)

(73) Assignee: Cardiovascular Imaging Technologies L.L.C., Kansas City, MO (US)

( * ) Notice: Subject to any disclaimer, the term of this patent is extended or adjusted under 35 U.S.C. 154(b) by 140 days.

(21) Appl. No.: 12/119,202

(22) Filed: May 12, 2008

(65) Prior Publication Data

US 2008/0277587 A1    Nov. 13, 2008

Related U.S. Application Data

(60) Provisional application No. 60/917,278, filed on May 10, 2007.

(51) Int. Cl.
*G01D 18/00* (2006.01)
(52) U.S. Cl. .................................. 250/252.1
(58) Field of Classification Search ................ 250/252.1
See application file for complete search history.

(56) References Cited

U.S. PATENT DOCUMENTS

2007/0075248 A1*   4/2007   Case et al.   ............... 250/363.01

OTHER PUBLICATIONS

Ichihara T., Ogawa K., Motomura N., Kubo A., Hashimoto S.; Compton Scatter Compensation Using the Triple-Energy Window Method for Single and Dual Isotope SPECT; Dec. 1993; The Journal of Nuclear Medicine; vol. 34, No. 12; pp. 2216-2221.*
Du Y., Stumpf M., Frey E.; Efficient Monte Carlo Based Scatter Estimation for SPECT Imaging with Photon Track Reuse; May 1, 2007; The Journal of Nuclear Medicine; vol. 48, Supplement 2; p. 334.*

* cited by examiner

*Primary Examiner* — David P Porta
*Assistant Examiner* — David S Baker
(74) *Attorney, Agent, or Firm* — Hovey Williams LLP (57) ABSTRACT

A method and apparatus for correcting scattering in SPECT I-123 imaging. The method generally includes: accessing list mode data for a plurality of pixels corresponding to a first SPECT I-123 image generated using a gamma camera; generating a raw energy spectrum for at least some of the pixels utilizing the acquired list mode data; acquiring a gamma camera model corresponding to the gamma camera; utilizing the gamma camera model and an iterative algorithm to apply a first scattering correction to the raw energy spectrum; utilizing a Compton window to apply a second scattering correction to the raw energy spectrum; and generating a correction table with the corrected raw energy spectrum.

21 Claims, 7 Drawing Sheets

METHOD AND APPARATUS FOR CORRECTING SCATTERING IN SPECT IMAGING

RELATED APPLICATION

This nonprovisional patent application claims priority benefit, with regard to all common subject matter, of earlier-filed U.S. provisional patent application titled "METHOD AND APPARATUS FOR CORRECTING SCATTERING IN SPECT IMAGING", Ser. No. 60/917,278, filed May 10, 2007. The identified earlier-filed application is hereby incorporated by reference in its entirety into the present application.

BACKGROUND OF THE INVENTION

1. Field of the Invention

Embodiments of the present invention relate to methods and apparatuses for correcting scattering in SPECT imaging. More particularly, various embodiments of the present invention correct scattering in SPECT I-123 images by utilizing an iterative algorithm and a Compton window.

2. Description of the Related Art

Single photon emission computed tomography (SPECT) imaging is a popular nuclear medicine imaging technique operable to generate three-dimensional information through the detection of gamma rays. SPECT imaging is often utilized to perform Myocardial perfusion imaging (MPI) to facilitate in the detection of cardiovascular defects. Various radioisotopes are typically employed with SPECT imaging, including Technetium-99m (Tc-99m) and Thalium-201 (Tl-201).

Iodine-123 (I-123) is being widely investigated for various cardiac molecular imaging applications as an alternative to Tc-99m and Tl-201. However, the low-energy high resolution (LEHR) collimators typically employed by cardiac laboratories are unable to stop high-energy (e.g., 529 keV) I-123 emissions, thereby resulting in photopeak scattering and the degradation of spatial uniformity. As such, the usage of I-123 in SPECT imaging is often significantly limited by photopeak scattering.

SUMMARY OF THE INVENTION

Embodiments of the present invention solve the above-described problems and provide a distinct advance in the art of SPECT scattering correction. More particularly, various embodiments of the present invention correct scattering in SPECT I-123 images by utilizing an iterative algorithm and a Compton window and a number of finely sampled Compton scatter windows near the photopeak energy.

In various embodiments, a method of correcting scattering in SPECT I-123 imaging is provided. The method generally includes: accessing highly sampled photon energy data corresponding to a first SPECT I-123 image generated using a gamma camera; generating a raw energy spectrum for at least some of the pixels utilizing the highly sampled photon energy data; acquiring a gamma camera model corresponding to the gamma camera; utilizing the gamma camera model and an iterative algorithm to apply a first scattering correction to the raw energy spectrum; utilizing a Compton window to apply a second scattering correction to the raw energy spectrum; and generating a correction table with the corrected raw energy spectrum. In some embodiments, the correction table may be utilized to correct a second SPECT I-123 image.

Other aspects and advantages of the present invention will be apparent from the following detailed description of the embodiments and the accompanying drawing figures. It is to be understood that both the foregoing general description and the following detailed description are exemplary and explanatory only and are not necessarily restrictive of the invention claimed. The accompanying drawings, which are incorporated in and constitute a part of the specification, illustrate embodiments of the invention and together with the general description, serve to explain the principles of the invention.

BRIEF DESCRIPTION OF THE DRAWING FIGURES

Embodiments of the present invention is described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of various embodiments of the invention references the accompanying drawings which illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Figure 1:
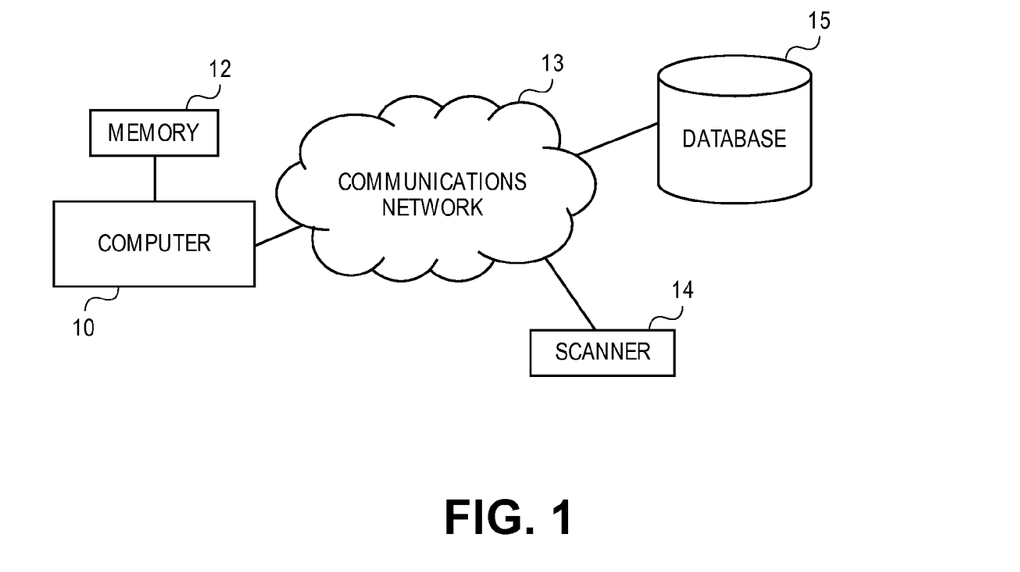
FIG. 1 is a block diagram of a system constructed in accordance with various embodiments of the present invention.
Figure 2:
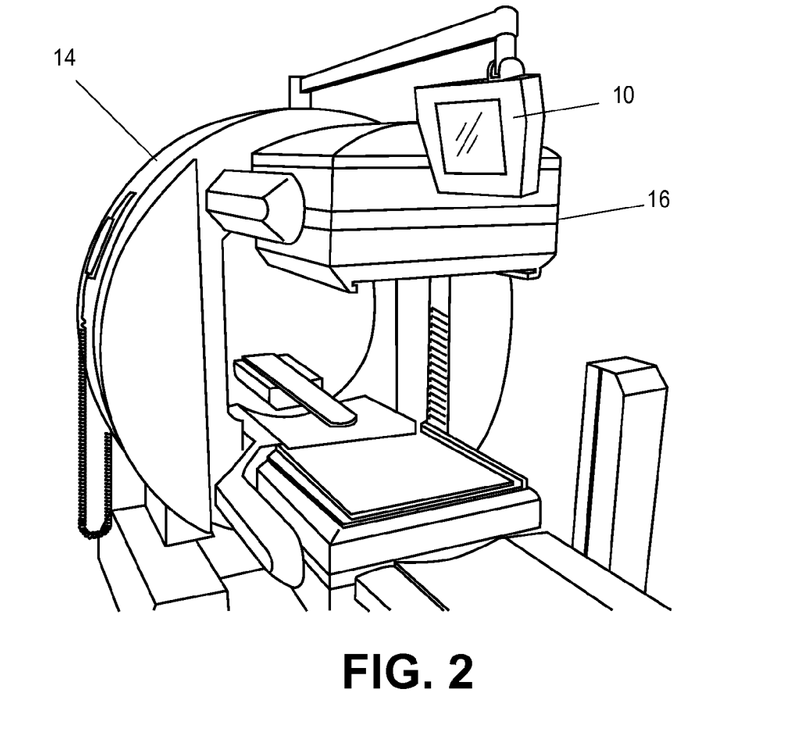
FIG. 2 is a perspective view of a computing device coupled with a SPECT scanner.

Methods consistent with the present teachings are especially well-suited for implementation by a computing element, such as the computer 10 illustrated in FIGS. 1 and 2. The computer 10 can include various analog and digital components operable to perform the various functions discussed herein. In some embodiments, the computer 10 can include a microprocessor, a microcontroller, a programmable logic device, an application specific integrated circuit, digital and analog logic devices, computing elements such as personal computers, servers, computing networks, portable computing devices, combinations thereof, and the like. Thus, the computer 10 can comprise a plurality of computing elements in some embodiments. The computer 10 may include or be associated with a memory 12. The memory 12 may include memories of any form or configuration for storing computer programs and information, as is discussed in more detail below. Thus, the memory 12 can comprise a computer-readable medium.

Some embodiments of the present invention may provide a computer program. The computer program may comprise instructions for implementing functions in one or more computing devices such that the program is not limited to functioning and/or controlling only the computer 10. The program may also comprise various code segments, which each may include one or more instructions, one or more instruction lists, only a portion of an instruction list, and/or only a portion of an instruction. Code segments may include overlapping lists of instructions—that is, a first code segment may include at least portions of instructions A and B, and a second code segment may include at least portions of instructions B and C. Each code segment may be embodied as human-readable source code or script, as machine-readable object code, and/or as one or more machine-executable files such as compiled source code. Further, the computer program may comprise one or more computer programs each including any number of code segments to perform any of the functions disclosed herein.

The computer program may be stored in or on at least one computer-readable medium accessible by one or more computing devices, such as the computer 10, to enable one or more computing devices to implement the various functions of the computer program. In the context of this application, a "computer-readable medium" can be any element or combination of elements that can contain, store, communicate, propagate or transport at least a portion of the program for use by or in connection with one or more computing devices such as the computer 10.

The computer-readable medium can be, for example, but is not limited to, an electronic, magnetic, optical, electromagnetic, infrared, or semi-conductor system, apparatus, device, or propagation medium operable for use by the computer 10 or other devices. More specific, although not inclusive, examples of the computer-readable medium may include the following: an electrical connection having one or more wires, a portable computer diskette, a random access memory (RAM), a read-only memory (ROM), an erasable, programmable, read-only memory (EPROM or flash memory), an optical fiber, a portable compact disc (CD), a digital video disc (DVD, HD-DVD, Blu-Ray), and an electrical signal representing one or more portions of the computer program. The computer-readable medium could even be paper or another suitable medium upon which the program is printed, as the program can be electronically captured, via for instance, optical scanning of the paper or other medium, then compiled, interpreted, or otherwise processed in a suitable manner, if necessary, and then stored in a computer memory. In some embodiments, the computer program is stored on the memory 12 associated with the computer 10.

However, embodiments of the present invention may be implemented in hardware, software, firmware, and/or combinations thereof and are not limited to the computer program discussed herein. The computer program and associated equipment are merely examples of a program and equipment that may be used to implement embodiments of the present invention and may be replaced with other software and/or equipment without departing from the scope of the present teachings.

As shown in FIG. 1, the computer 10 may be directly or indirectly coupled with a scanner 14 to facilitate I-123 scattering correction as is discussed in more detail below. For example, the computer 10 may be coupled with the scanner 14 utilizing a wired connection and/or by indirectly coupling with the scanner 14 through a communications network 13 such as the internet. Data utilized by the computer 10 may also be stored and retrieved from a database 15, which may be accessed directly or through the communications network 13.

The scanner 14 is a single photon emission computed tomography (SPECT) scanner including a gamma camera 16, shown in FIG. 2, operable to detect gamma rays. The gamma camera 16 may be rotated at least partially around a source object, such as a patient, to detect gamma rays emitted by I-123 from a plurality of angles. In some embodiments, the gamma camera 16 may be operable to rotate 180 and/or 360 degrees around the patient.

Figure 3:
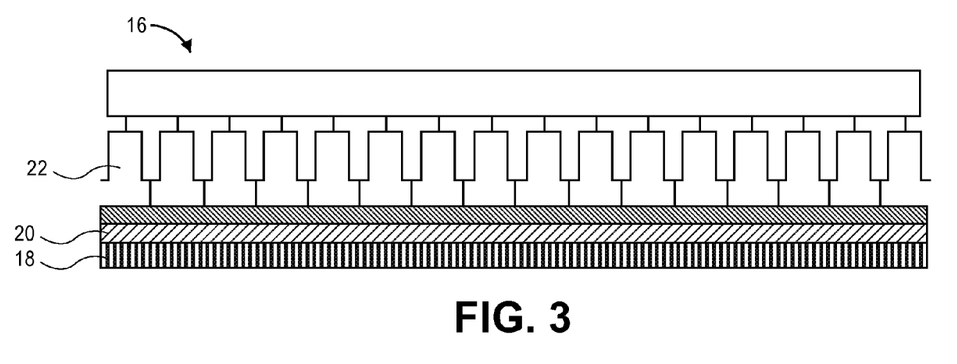
FIG. 3 is a schematic diagram of an exemplary gamma camera operable to be employed by the SPECT scanner of FIG. 1.

An exemplary gamma camera 16 operable to be utilized by the scanner 14 is illustrated in FIG. 3. The exemplary gamma camera 16 includes a low-energy high resolution (LEHR) collimator 18, a layer of sodium iodide crystal with thallium doping 20, and a plurality of photodetectors 22. The collimator 18 is positioned between the crystal 20 and the patient and is operable to at least partially limit the photons that may pass to the crystal 20 in a generally conventional manner. The crystal 20 and photodetectors 22 form a matrix of gamma detectors that are each operable to detect an emitted gamma ray. In some embodiments, the gamma camera 16 may present a 64×64 or 128×128 pixel configuration. However, embodiments of the present invention may utilize matrices and pixel configurations of any size.

Emitted gamma photons of the particular source orientation defined by the collimator 18 pass through the apertures of the collimator 18 and strike the crystal 20. The crystal 20 scintillates in response to the gamma photons and produces a flash of light in general proximity to the location of the photon-crystal collision. The photodetectors 22 are positioned behind the crystal 20 and are operable to detect the intensity of the light and its corresponding pixel location.

Thus, for each position of the gamma camera 16, the scanner 14 is operable to generate data corresponding to the pixel location and intensity of each detected gamma ray. Further, as should be appreciated by those skilled in the art, the gamma camera 16 is operable to detect a plurality of gamma rays (counts) at each position. The scanner 14 is operable to generate highly sampled photon energy data, such as list mode data, corresponding to the detected gamma rays at one or more positions of the gamma camera 16. For example, for each of the 64×64 pixels, the generated list mode data may represent the number of gamma rays detected and their corresponding energies. Thus, in some embodiments, the scanner 14 is operable to generate list mode data for each pixel and camera position in form of (x, y, E) where (x, y) represents a pixel coordinate and E represents gamma photon energy (in keV for example).

It should be appreciated that the computer 10 and scanner 14 need not be directly coupled as the scanner 14 may be operable to store list mode data on an intermediate device, such as a second computer or internal medium, from which the computer 10 may access the data. Further, it should be appreciated that the computer 10 and the scanner 14 may be integral with each other such that the computer 10 may be operable to provide conventional transmission, diagnosis, computing, and processing functions in addition to the methods and functions disclosed herein.

Figure 10:
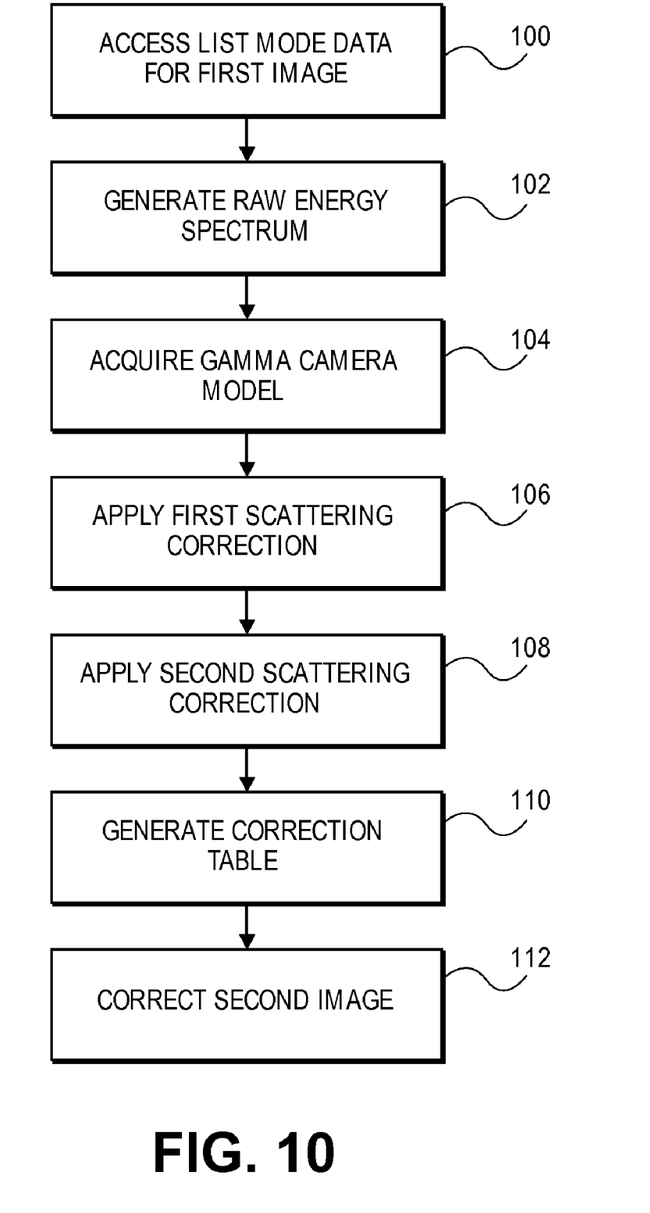
FIG. 10 is a block diagram illustrating various functions operable to be performed by various embodiments of the present invention.

A flowchart of steps that may be utilized by embodiments of the present invention to correct SPECT I-123 scattering is illustrated in FIG. 10. Some of the blocks of the flow chart may represent a module segment or portion of code of the computer program of embodiments of the present invention which comprises one or more executable instructions for implementing the specified logical function or functions.

In some alternative implementations, the functions noted in the various blocks may occur out of the order depicted in FIG. 10. For example, two blocks shown in succession in FIG. 10 may in fact be executed substantially concurrently, or the blocks may sometimes be executed in the reverse order depending upon the functionality involved. Further, any combination of the steps illustrated in FIG. 10 may be performed by embodiments of the present invention and one or more of the steps may be omitted by various embodiments of the present invention.

The steps illustrated in FIG. 10 generally include: accessing highly sampled photon energy data, referenced as step 100; generating a raw energy spectrum 24, referenced as step 102; acquiring a gamma camera model 26, referenced as step 104; applying a first scattering correction, referenced as step 106; applying a second scattering correction, referenced as step 108; generating a correction table, referenced as step 110; and correcting an image, referenced at step 112.

In step 100, the computer 10 accesses highly sampled photon energy data for a plurality of pixels corresponding to a first SPECT Iodine-123 (I-123) image generated using the gamma camera 16. The steps of the method disclosed herein may apply to highly sampled photon energy data other than list mode data that may be generated by other cameras or other pieces of equipment. Multiple window energy sampling may be used to generate highly sampled photon energy date. However, to illustrate the steps of the method, list mode data is used as an example. "List mode data," as utilized herein, refers to data that indicates the pixel location and energy of a detected gamma ray. As discussed above, the scanner 14 may generate the list mode data in a generally conventional manner by detecting gamma rays emitted by I-123 disposed within a patient or any other source object. However, the list mode data accessed in step 100 may be generated in any fashion to indicate the pixel location and energy of a detected gamma ray.

In some embodiments, the computer 10 may access the list mode data by accessing the memory 12. Additionally or alternatively, the computer 10 may access the list mode data by directly or indirectly coupling with the scanner 14 and acquiring data therefrom. The computer 10 may also acquire the list mode data from other sources, such as from another computing device 10, database 15, or data repository. For example, the computer 10 may access a database 15 through the internet or another communications network 13 to access the list mode data in step 100. The list mode data accessed by the computer 10 in step 100 may be stored within the memory 12 for later access and processing by the computer 10.

In step 102, the computer 10 generates a raw energy spectrum 24 utilizing the list mode data accessed in step 100. In various embodiments, the computer 10 generates a raw energy spectrum 24 for each pixel corresponding to the SPECT I-123 list mode data accessed in step 100. Thus, for example, where the gamma camera 16 presents a 64×64 pixel matrix, the computer 10 generates a raw energy spectrum 24 for each of the 64×64 pixels based on the accessed list mode data. To generate the raw energy spectrum 24 for each pixel, the computer 10 may aggregate the number of gamma rays (counts) detected at each energy value. Exemplary raw energy spectrums 24 for one pixel are illustrated in FIGS. 4 and 5, where the 159 keV peak associated with I-123 is clearly visible.

Figure 4:
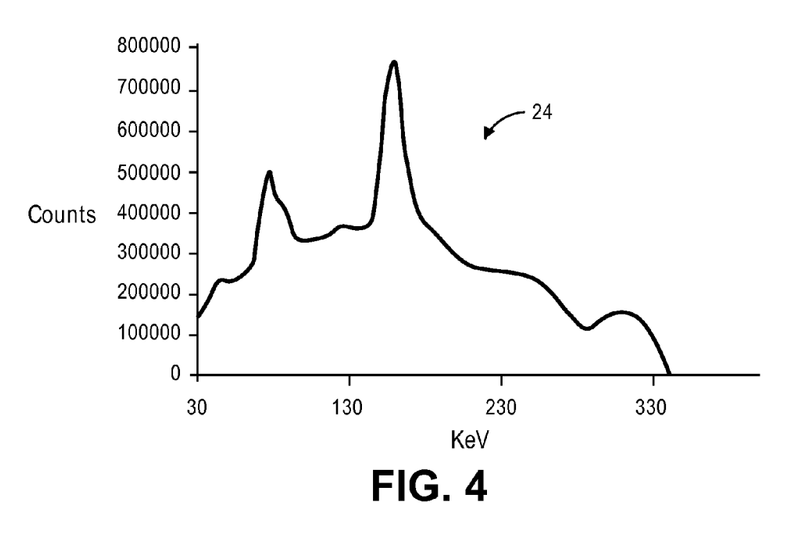
FIG. 4 is a graph of an exemplary raw I-123 energy spectrum.
Figure 5:
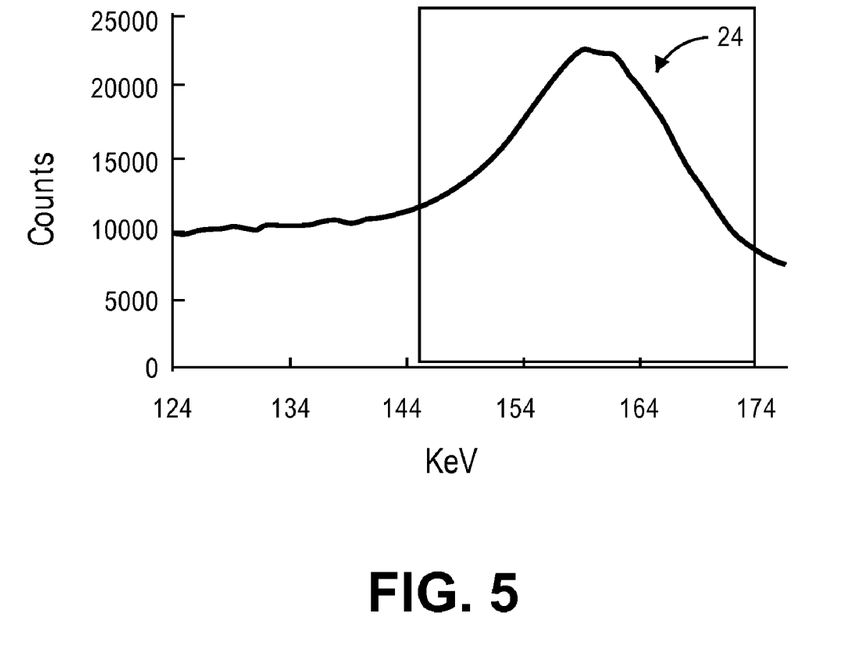
FIG. 5 is a graph of the exemplary raw I-123 energy spectrum of FIG. 3 showing portions of the spectrum in more detail.

The exemplary raw energy spectrums 24 illustrated in FIGS. 4 and 5 include the effects of photopeak scattering and down scattering. Photopeak scattering is caused by high-energy (approximately 556 keV) I-123 gamma rays penetrating the collimator 18, regardless of the configuration of the collimator's apertures, and striking the crystal 20 to create a flash of light. These stray high-energy I-123 gamma rays originating from angles different than those defined by the collimator 18 produce energy spectrums that erroneously indicate counts and associated energy levels. In a situation while scattered photons contribute a substantial portion of overall counts, image uniformity and contrast can be highly degraded and diagnostic accuracy can be lost. Down scattering is caused by the deflection of 159 keV I-123 gamma rays off of electrons in the patient and reduces the energy levels detected by the gamma camera 16, thereby also producing energy spectrums that erroneously indicate counts and associated energy levels.

The raw energy spectrums 24 may be represented by the computer 10 in a listing or table form, such as within a listing of the number of counts associated with each energy value. Thus, the raw energy spectrums 24 are not necessarily represented in graphical format by the computer 10 as the spectrum illustrated in FIGS. 4 and 5 is merely exemplary. The raw energy spectrums 24 for each of the pixels may be stored by the computer 10 in the memory 12 for later access and processing. Additionally or alternatively, the computer 10 may provide the raw energy spectrums 24 to other devices and systems through a communications network 13 or direct connections.

Although it is generally desirable to maximize the number of pixels utilized to form the list mode data and raw energy spectrums 24, in some embodiments, the computer 10 may generate raw energy spectrums 24 for only some of the pixels presented by the gamma camera 16 to conserve computing and memory resources.

Further, in some embodiments, the computer 10 may generate the raw energy spectrums 24 by accessing raw energy spectrums 24 previously generated by the computer 10 or other devices. For example, the computer 10 may access the memory 12 and/or other databases 15 and computing devices to retrieve the various energy spectrums. Thus, a first computing device could perform step 100 to access the list mode data and a second computing device could generate the raw energy spectrums 24 by accessing the data retained by the first computing device.

In step 104, the computer 10 acquires a gamma camera model 26 corresponding to the gamma camera 14 utilized to generate the list mode data accessed in step 100. The gamma camera model 26 represents the response of the gamma camera 14 to the measurement of relatively pure energy sources. As is discussed in more detail below, the gamma camera model 26 is utilized to perform the first scattering correction.

Figure 6A:
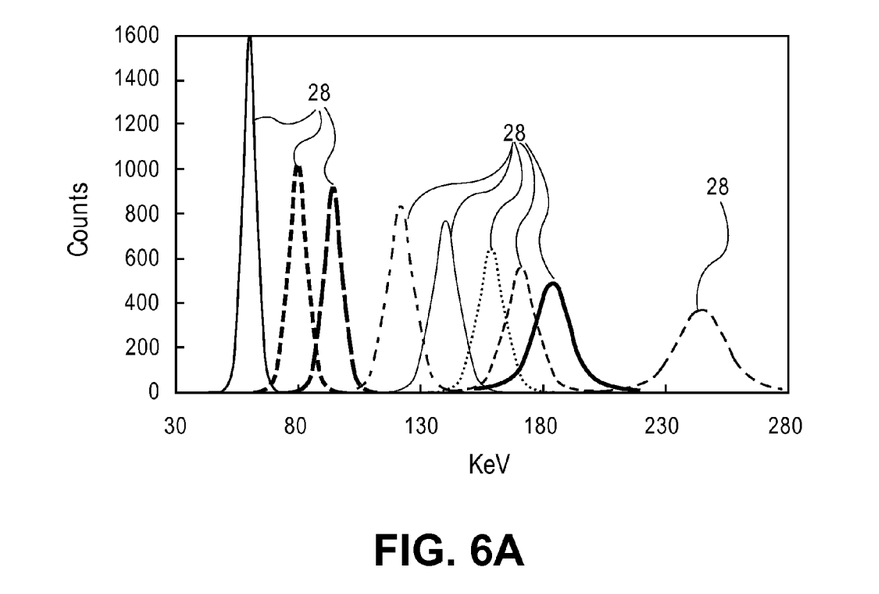
FIG. 6A is a graph showing various exemplary measurements of relatively pure energy sources.
Figure 6B:
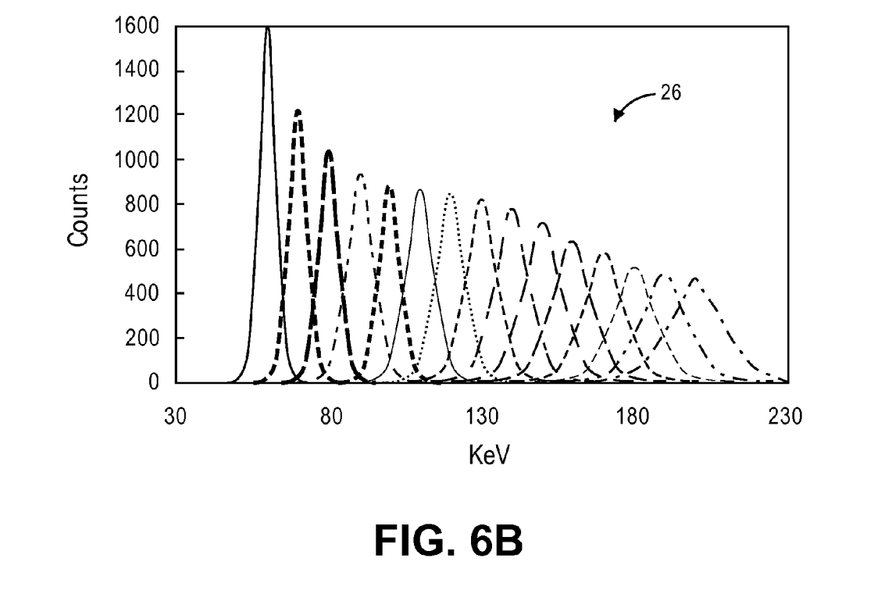
FIG. 6B is a graph showing an exemplary gamma camera model generated from the measurements of FIG. 6A.

An exemplary gamma camera model 26 is presented by FIGS. 6A and 6B, which illustrate the response of the gamma camera 14 to a plurality of gamma rays having energies in the range of 30 keV to 230 keV. In some embodiments, the gamma rays may be measured utilizing the energy impulse response (EIR) conventionally provided by the gamma camera 14 to directly measure the energy response of the gamma camera 14 to various energy sources. To acquire the gamma camera model 26, the individual EIR in various energy channels may be sampled and the counts of each channel may be normalized to the total number of counts.

Direct measurement of EIRs is generally limited to few energies because only a finite number of energy sources are available in the desired energy range (e.g. from 50 to 200 keV). To overcome this problem, the measured EIRs 28 may be extrapolated to generate other EIRs and form a complete model 26. For example, seven sources with nine different energies may be utilized as initial EIR measurements: Am-241(60 keV), Ba-133(81 keV), Ga-67(94 keV, 184 keV), Co-57(122 keV), Tc-99m (140 keV) I-123 (159 keV) and In-111(171 keV, 245 keV). The response by the camera 16 to each energy level is measured to generate the EIR 28 and plotted as shown in FIG. 6A. To complete the model 26, additional data is extrapolated from the measured data and plotted as shown in FIG. 6B. The measured EIRs may be extrapolated utilizing various mathematical methods, including the normalization discussed above, to enable the gamma camera model 26 to represent an entire spectrum of energies.

The gamma camera model 26 generated in step 104 will be generally similar for all cameras of the same model. For example, if first and second gamma cameras are both SIEMENS ECAM SPECT systems, the gamma camera model 26 for the first and second gamma cameras will be generally similar. Thus, in some embodiments, step 104 may only be performed once for any particular camera model and the resulting gamma camera model 26 may be stored within the memory 12 for later use.

In particular, in some embodiments a database 15 of gamma camera models 26 may be formed corresponding to commonly used gamma cameras such that the gamma camera model 26 may be acquired by the computer 10 in step 104 by accessing the database 15. As such, it is not necessary in all embodiments to generate the gamma camera model 26 by directly measuring EIRs. However, it may be desirable in some embodiments to generate a gamma camera model 26 for each utilized gamma camera in the event a particular gamma camera includes defects or provides non-conforming functionality.

In step 106, a first scattering correction is applied to at least some of the raw energy spectrums 24 generated in step 102. The first scattering correction is applied by the computer 10 by utilizing the gamma camera model 26 generated in step 104 and an iterative algorithm. The iterative algorithm utilized in this step may be any one of a family of mathematical algorithms that operate on energy spectrum data to correct for scattering. The iterative algorithm, such as the maximum likelihood optimizer described below, provides an iterative energy spectrum deconvolution that is operable to improve the energy resolution of the gamma camera 14 to correct for scattering.

The raw energy spectrums 24 may be regarded as a linear combination of energy components that are from photopeak and scatter photons. Thus, if this spectrum is sampled by energy channels, the counts in each sample point can be assumed as a series of energy components convolved with probability functions which correlate energy components to energy channels. Such an assumption is given as:

$$S_i = \sum_j P_{ij} e_j, \qquad \text{EQ. 1}$$

where $S_i$ represents counts of an energy spectrum sampled in ith energy channel, $e_j$ is jth energy component and $\{P_{ij}\}$ is the probability of jth energy component correlating to ith energy channel.

As a scintillation system, the detection provided by the gamma camera 14 and in some embodiments, the emission of gamma photons can both be modeled as Poisson process, thus a log likelihood function of system can be created from the energy spectrum. This function is given as:

$$L_S(e) = \left\{ \sum_{i,j} -P_{ij} e_j + X_{ij} \ln P_{ij} e_j - \log X_{ij}! \right\}, \text{ and} \qquad \text{EQ. 2}$$

$$X = P_{ij} e_j \qquad \text{EQ. 3}$$

By utilizing the gamma camera model 26 generated in step 104, the iterative algorithm may utilize the knowledge of the energy components of an energy spectrum to perform scatter correction by excluding scatter components out of a narrow energy window (several keVs), which is equivalently to include energy components near I-123 photopeaks only. By applying E-step (expectation) and M-step (maximization), the iterative algorithm can be derived as:

$$e_j^{new} = \frac{e_j^{old}}{\sum_i P_{ij}} \sum_i P_{ij} \frac{S_i}{\sum_k P_{ik} e_k^{old}}, \qquad \text{EQ. 4}$$

where $S_i$ represents counts of an energy spectrum sampled in an ith energy channel, $e_j^{old}$ is an initial jth energy component, $P_{ij}$ is the probability of jth energy component correlating to ith energy channel, $P_{ik}$ is the probability of kth energy component correlating to ith energy channel, and $e_j^{new}$ is a corrected jth energy component. Thus, the iterative algorithm represents counts in an energy channel as a linear combination of energy components and the iterative algorithm solves the inverse problem to estimate energy components sampled in various energy channels. As the algorithm iteratively moves forward, each energy component eventually converges to a fixed value. Additional information concerning application of the iterative algorithm is provided by the following materials.

In step 108, a Compton window is utilized to apply a second scattering correction to the raw energy spectrum. In some embodiments, the Compton window of step 108 may be applied after the first correction of step 106. However, in other embodiments, step 108 may be performed before or concurrently with step 106.

Figure 7:
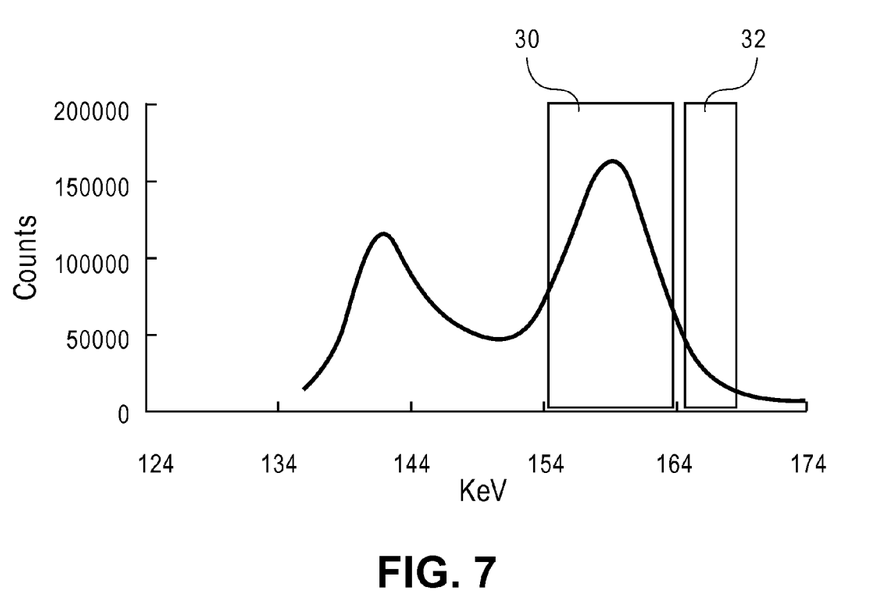
FIG. 7 is a graph showing an exemplary corrected I-123 energy spectrum generated by various embodiments of the present invention.

Generally, the Compton window includes window A 30 and window B 32, as seen in FIG. 7. Window A 30 is centered around the I-123 159 keV peak +/-3% keV. Window B 32 is a fixed 4 keV window. The second correction is applied by taking window A 30 minus the product of C and Window B 32, where C is a scale factor.

In step 110, a correction table is generated with the corrected raw energy spectrum resulting from steps 106 and 108. The correction table embodies the corrections made in steps 106 to 108 to the raw energy spectrum 24 based on the gamma camera model 26 and allows the computer 10 to correct additional SPECT I-123 images as is discussed below in step 112.

Figure 8:
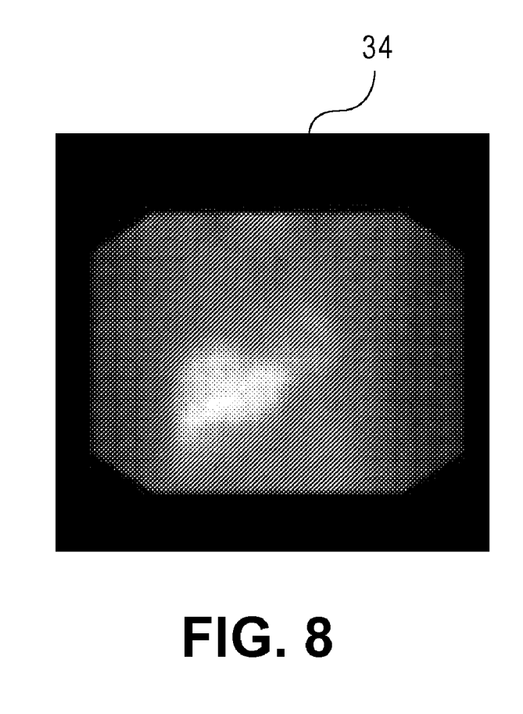
FIG. 8 is an exemplary I-123 image that is uncorrected.
Figure 9:
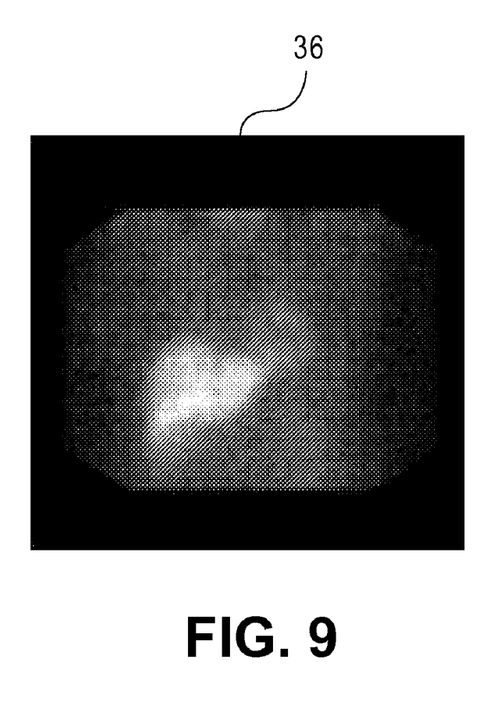
FIG. 9 is an exemplary I-123 image that has been corrected.

In step 112, the correction table generated in step 110 is utilized to correct one or more SPECT I-123 images, as shown in FIGS. 8 and 9. FIG. 8 shows an uncorrected SPECT I-123 image 34, while a corrected image 36 is seen in FIG. 9. The correction table may be utilized to correct the SPECT I-123 image that was utilized to generate the raw energy spectrum 24 and/or to other SPECT I-123 images to correct for photopeak scattering and down scattering. For example, the raw energy spectrum 24 may be generated from a first SPECT I-123 image and the correction table may be utilized to correct any number of additional SPECT I-123 images. Thus, in some embodiments, steps 100-110 may be performed once to generate the correction table and step 112 may be repeated for every additional SPECT I-123 image generated by the scanner 14.

It is believed that embodiments of the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

Having thus described various embodiments of the invention, what is claimed as new and desired to be protected by Letters Patent includes the following:

1. A method of correcting scattering in SPECT I-123 imaging, the method comprising:
   a) accessing highly sampled photon energy data for a plurality of pixels corresponding to a first SPECT I-123 image generated using a gamma camera;
   b) generating, using a microprocessor, a raw energy spectrum for at least some of the pixels utilizing the acquired highly sampled photon energy data;
   c) acquiring a gamma camera model corresponding to the gamma camera;
   d) applying, using the microprocessor, a first scattering correction to the raw energy spectrum that utilizes the gamma camera model and an iterative algorithm given by $$e_j^{new} = \frac{e_j^{old}}{\sum_i P_{ij}} \sum_i P_{ij} \frac{S_i}{\sum_k P_{ik} e_k^{old}}$$

where $S_i$ represents counts of an energy spectrum sampled in an ith energy channel, $e_j^{old}$ is an initial jth energy component, $P_{ij}$ is the probability of jth energy component correlating to ith energy channel, $P_{ik}$ is the probability of kth energy component correlating to ith energy channel, and $e_j^{new}$ is a corrected jth energy component;
   e) applying, using the microprocessor, a second scattering correction to the raw energy spectrum utilizing a Compton window; and
   f) generating, using the microprocessor, a correction table with the corrected raw energy spectrum.

2. The method of claim 1, wherein the first and second scattering correction at least partially corrects photopeak scatter and downscatter.

3. The method of claim 1, wherein the highly sampled photon energy data is list mode data.

4. The method of claim 1, wherein the raw energy spectrum for a pixel is generated by aggregating the highly sampled photon energy data for the pixel.

5. The method of claim 1, wherein the gamma camera model is acquired from a computer-readable database.

6. The method of claim 1, wherein the gamma camera model is acquired by measuring a plurality of elements with the gamma camera.

7. The method of claim 1, further including utilizing the correction table to correct a second SPECT I-123 image.

8. A non-transitory computer-readable storage medium with an executable program thereon, wherein the program instructs a microprocessor to correct scattering in SPECT-123 imaging according to the steps of:
   accessing highly sampled photon energy data for a plurality of pixels corresponding to a first SPECT I-123 image generated using a gamma camera;
   generating a raw energy spectrum for at least some of the pixels utilizing the acquired highly sampled photon energy data;
   acquiring a gamma camera model corresponding to the gamma camera;
   utilizing the gamma camera model and an iterative algorithm to apply a first scattering correction to the raw energy spectrum, the iterative algorithm given by $$e_j^{new} = \frac{e_j^{old}}{\sum_i P_{ij}} \sum_i P_{ij} \frac{S_i}{\sum_k P_{ik} e_k^{old}}$$

where $S_i$ represents counts of an energy spectrum sampled in an ith energy channel, $e_j^{old}$ is an initial jth energy component, $P_{ij}$ is the probability of jth energy component correlating to ith energy channel, $P_{ik}$ is the probability of kth energy component correlating to ith energy channel, and $e_j^{new}$ is a corrected jth energy component;
   utilizing a Compton window to apply a second scattering correction to the raw energy spectrum; and
   generating a correction table with the corrected raw energy spectrum.

9. The computer program of claim 8, wherein the first and second scattering correction at least partially corrects photopeak scatter and downscatter.

10. The computer program of claim 8, wherein the highly sampled photon energy data is list mode data.

11. The computer program of claim 8, wherein the raw energy spectrum for a pixel is generated by aggregating the highly sampled photon energy data for the pixel.

12. The computer program of claim 8, wherein the gamma camera model is acquired from a computer-readable database.

13. The computer program of claim 8, wherein the gamma camera model is acquired by measuring a plurality of elements with the gamma camera.

14. The computer program of claim 8, further including utilizing the correction table to correct a second SPECT I-123 image.

15. A system operable to correcting scattering in SPECT I-123 imaging, the system comprising:
   a SPECT scanner having a gamma camera; and
   a computing element coupled with the SPECT scanner and operable to
   access the SPECT scanner to acquire highly sampled photon energy data for a plurality of pixels corresponding to a first SPECT I-123 image generated using the gamma camera,
   generate a raw energy spectrum for at least some of the pixels utilizing the acquired highly sampled photon energy data,
   acquire a gamma camera model corresponding to the gamma camera, utilize the gamma camera model and an iterative algorithm to apply a first scattering correction to the raw energy spectrum, the iterative algorithm given by $$e_j^{new} = \frac{e_j^{old}}{\sum_i P_{ij}} \sum_i P_{ij} \frac{S_i}{\sum_k P_{ik} e_k^{old}}$$

where $S_i$ represents counts of an energy spectrum sampled in an ith energy channel, $e_j^{old}$ is an initial jth energy component, $P_{ij}$ is the probability of jth energy component correlating to ith energy channel, $P_{ik}$ is the probability of kth energy component correlating to ith energy channel, and $e_j^{new}$ is a corrected jth energy component, utilize a Compton window to apply a second scattering correction to the raw energy spectrum, and generate a correction table with the corrected raw energy spectrum.

16. The system of claim 15, wherein the first and second scattering correction at least partially corrects photopeak scatter and downscatter.

17. The system of claim 15, wherein the highly sampled photon energy data is list mode data.

18. The system of claim 15, wherein the raw energy spectrum for a pixel is generated by aggregating the highly sampled photon energy data for the pixel.

19. The system of claim 15, wherein the gamma camera model is acquired from a computer-readable database associated with the computing element.

20. The system of claim 15, wherein the gamma camera model is acquired by measuring a plurality of elements with the gamma camera.

21. The system of claim 15, wherein the computing element is further operable to utilize the correction table to correct a second SPECT I-123 image.

* * * * *